US005287847A

United States Patent [19]

Piper et al.

[11] Patent Number: 5,287,847
[45] Date of Patent: Feb. 22, 1994

[54] UNIVERSAL NEBULIZER

[75] Inventors: Samuel D. Piper, Sacramento; Otto G. Raabe, Davis; James I. C. Lee; Gordon A. Wong, both of Sacramento, all of Calif.

[73] Assignee: Vortran Medical Technology, Inc., Sacramento, Calif.

[21] Appl. No.: 919,810

[22] Filed: Jul. 24, 1992

[51] Int. Cl.[5] ............................................. A61M 16/00

[52] U.S. Cl. ........................... 128/200.21; 128/200.18

[58] Field of Search ...................... 128/200.18, 200.14, 128/200.12, 200.24, 203.12, 204.25

[56] References Cited

U.S. PATENT DOCUMENTS

| | | | |
|---|---|---|---|
| 1,294,246 | 2/1919 | Dorment | 239/338 |
| 1,887,949 | 11/1932 | Schmitt | 239/135 |
| 2,069,455 | 2/1937 | Massa | 239/338 |
| 2,369,183 | 1/1939 | Cameto | 112/98 |
| 2,709,577 | 5/1955 | Pohndorf et al. | 261/2 |
| 2,726,896 | 12/1955 | McKinnon | 239/335 |
| 2,740,665 | 4/1956 | Dorsak et al. | 239/371 |
| 2,785,679 | 3/1957 | Wullschleger | 128/200.18 |
| 2,882,026 | 4/1959 | Eichelman | 128/200.14 X |
| 3,084,874 | 4/1963 | Jones et al. | 239/8 |
| 3,097,645 | 7/1963 | Lester | 128/200.21 |
| 3,512,718 | 5/1970 | Cranage | 239/338 |
| 3,664,337 | 5/1972 | Lindsey et al. | 128/200.18 |
| 3,744,722 | 7/1973 | Burns | 239/338 |
| 3,762,409 | 10/1973 | Lester | 128/200.14 |
| 4,177,945 | 12/1979 | Schwartz | 239/338 |
| 4,333,450 | 6/1982 | Lester | 128/200.14 |
| 4,560,519 | 12/1985 | Cerny | 261/78 A |
| 4,566,452 | 1/1986 | Farr | 128/200.21 |
| 4,588,129 | 5/1986 | Shanks | 239/338 |
| 4,635,857 | 1/1987 | Hughes | 239/690 |
| 4,832,012 | 5/1989 | Raabe et al. | 128/200.21 |
| 5,080,093 | 1/1992 | Raabe et al. | 128/203.12 |

FOREIGN PATENT DOCUMENTS

| | | | |
|---|---|---|---|
| 1528406 | 6/1968 | France | 128/200.18 |

*Primary Examiner*—Edgar S. Burr
*Assistant Examiner*—Eric P. Raciti
*Attorney, Agent, or Firm*—John P. O'Banion

[57] ABSTRACT

A nebulizer (10) for generating high concentrations of inhalable medicinal aerosols over a wide range of flow rates and mass outputs for medical inhalation therapy applications. A primary orifice (26), secondary orifice (44), inter-orifice gap (54), stagnation baffle (60), and spray gap (66) are scalable within defined parameters to provide any desired flow rate or mass output. The nebulizer is ideally suited for inhalation therapy of infants and children and can provide aerosols with flow rates ranging from less than 1 liter per minute to approximately 3 liters per minute at normal compressed gas pressures. The design parameters can also be scaled within defined limits to produce greater flows for treatment of adults or for use in other applications requiring high volumetric flow rates.

25 Claims, 5 Drawing Sheets

UNIVERSAL NEBULIZER

BACKGROUND OF THE INVENTION

1. Field of the Invention

This invention pertains generally to nebulizers for generating medicinal aerosols, and more particularly to a pneumatic nebulizing apparatus with fully scalable flow rates and output volumes which is suitable for delivering medicinal aerosol to neonates and children as well as to adults.

2. Description of the Background Art

Medical compressed-gas-operated nebulizers of various types have been widely used for inhalation delivery of aerosols containing medication or other constituents to the conductive airways of the lung and the gas exchange regions of the deep lung. Aerosols are relatively stable suspensions of finely divided droplets or solid particles in a gaseous medium, usually in air. When inhaled, aerosol particles may be deposited by contact upon the various surfaces of the respiratory tract leading to potential injury, desirable therapeutic action, or planned diagnostic behavior depending on the particular properties of the particles. Inhalable aerosols are those consisting of particles smaller than 10 micrometers in aerodynamic equivalent diameter.

Because of the high permeability of the lung and the copious blood flow, medications depositing in the lung can readily enter the blood for action throughout the body, while other medications can directly influence the airway epithelium and effect responses via various airway receptors. Properly generated and formulated aerosols can therefore be helpful in medical treatment. As tracers of airflow or indicators of lung responses, other types of aerosol particles deposited in the lung can also be a valuable diagnostic tool.

A nebulizer produces aerosols of fine particles by breaking a fluid into fine droplets and dispersing them into a flowing stream of gas. The droplet size from a medical nebulizer is considerably smaller than a conventional spray atomizer. Medical nebulizers are designed to convert water or aqueous solutions or colloidal suspensions to aerosols of fine, inhalable droplets that can enter the lungs of a patient during inhalation and deposit on the surface of the respiratory airways.

Pneumatic (compressed gas) medical nebulizers heretofore developed typically provide approximately 15 to 30 microliters of aerosol per liter of gas in finely divided droplets with volume or mass median diameters in the respirable range smaller than 4 micrometers. However, these nebulizers are optimized for treatment of adults utilizing volumetric flow rates greater than 3 liters of aerosol delivered per minute. For the treatment of children or infants, flow rates ranging from less than 1 liter per minute to approximately 3 liters per minute are desirable, since higher flow rates exceed the patient demand and cause improper treatment arrangements and considerable wasted aerosol.

Nebulizers optimized for treatment of adults are not scalable to provide for lower flow rates for use with infants and children. There is no known nebulizer available which can provide flow rates from less than 1 liter per minute to approximately 3 liters per minute when operated at normal gas pressures of approximately 103 to 343 kilopascals (15 to 50 pounds per square inch gauge pressure). As a result, it is necessary to reduce the gas pressure to use conventional nebulizers for treatment of infants and children. Doing so, however, results in incomplete nebulization of fluid and production of particles larger than 10 micrometers, which results in poor treatment of the patient.

Therefore, a need exists for a nebulizer which can provide flow rates from less than 1 liter per minute to approximately 3 liters per minute at normal gas pressures. The present invention satisfies that need and provides the further advantage of having scalable design parameters which permits any flow rate and output volume to be accommodated at normal gas pressures. By providing for high aerosol concentration and ideal particle size distribution at all flow rates, the present invention is suitable for treatment of adults, children, and infants.

SUMMARY OF THE INVENTION

The present invention generally pertains to a pneumatic nebulizer design which can be scaled to produce a family of nebulizers for generation of high concentrations of inhalable aerosols over a wide range of output flows for medical inhalation therapy applications. Not only can the present invention be scaled in physical size but, more importantly, its design parameters are scalable to provide for any specified flow rate or output volume when operated at normal gas pressures. The invention is ideally suited for generating medicinal aerosols at flow rates ranging from less than 1 liter per minute to approximately 3 liters per minute when operated at normal compressed gas pressures in the range from 103 to 343 kilopascals (15 to 50 pounds per square inch gauge pressure) and, therefore, operates at flow rates not achievable with conventional nebulizers. In addition, because of its unique design, there is no compromise of aerosol concentration or appropriateness of droplet size distribution, with output aerosol concentrations of up to 70 microliters of fluid aerosolized per liter of gas and volume median diameter of approximately 2.5 micrometers.

By way of example and not of limitation, the present invention employs a jet of gas flowing at the speed of sound to entrain and shatter a stream of fluid against a stagnation baffle proximal to the jet orifice. The expanding jet of gas produces a static pressure that is negative with respect to the ambient atmospheric pressure that is utilized to draw fluid via a feed tube into the jet stream and subsequently collides into the stagnation baffle that causes a violent disruption of the stream yielding up to a ten-fold increase in the mass concentration of inhalable droplets.

The present invention generally includes an injector assembly, a fluid pickup assembly, and a generally cylindrical stagnation baffle assembly. The jet of gas is forced through a cylindrical primary orifice in the nozzle assembly and expands as it passes through a larger diameter cylindrical secondary orifice chamber. This gas flow entrains and shatters a stream of fluid which is drawn through the fluid pickup assembly into the path of the expanding jet of gas such as occurs in a venturi system. The fluid stream is conducted to the inter-orifice gap by a pickup tube having one end immersed in a fluid reservoir. The fluid is drawn from the reservoir through the pickup tube into the jet stream and is thinned as it is sheared at the inlet surface of the second orifice. The droplets thus entrained in the gas stream subsequently collide with the stagnation baffle assembly which is oriented perpendicular to the direction of gas flow. The entrained fluid and gas stream is violently disrupted at the surface of the stagnation baffle thereby creating additional atomization of the fluid and yielding a high concentration of inhalable droplets of less than 4 micrometers in diameter.

The scalable design of the present invention permits a medical practitioner to choose a nebulizer which suits a particular application by specifying operating characteristics which include, but are not limited to: (a) volumetric rate of total gas flow carrying the aerosol produced in liters per minute; (b) mass output of inhalable aerosol in milligrams of fluid aerosol per minute; (c) droplet size distribution described by the mass median or volume median diameter in micrometer units of size; (d) volume of fluid required for proper operation ranging from a few milliliters to several hundred milliliters; and (e) maximum unattended operating time ranging from minutes to days. The present invention will provide the medical practitioner with a variable flow rate of high concentration inhalable aerosols with ideal droplet size distribution for efficient inhalation deposition in both the lung parenchyma and conducting bronchial airways. The apparatus will yield a high concentration of inhalable particles with mass or volume median size of 2.5 micrometers plus minus 1.0 micrometers with geometric standard deviation of approximately 2 plus or minus 0.4, and will produce aerosol with a density in the range of 35 to 50 microliters of fluid aerosol per liter of gas.

An object of the invention is to provide a nebulizer with a flow rates ranging from less than 1 liter per minute to approximately 3 liters per minute.

Another object of the invention is to provide a nebulizer which can operate at any flow rate or output volume when operated at a normal gas supply pressures ranging from 103 to 343 kilopascals (15 to 50 pounds per square inch gauge pressure).

Another object of the invention is to provide a nebulizer which is scalable to any desired flow rate.

Another object of the invention is provide a nebulizer which can provide aerosol output concentrations of up to 70 microliters per liter of gas.

Another object of the invention is to provide a nebulizer which can generate droplets of atomized fluid in the respirable size range with volumes or mass median diameters of less than 4 micrometers.

Another object of the invention is to provide a nebulizer wherein flow rate can be conveniently controlled.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
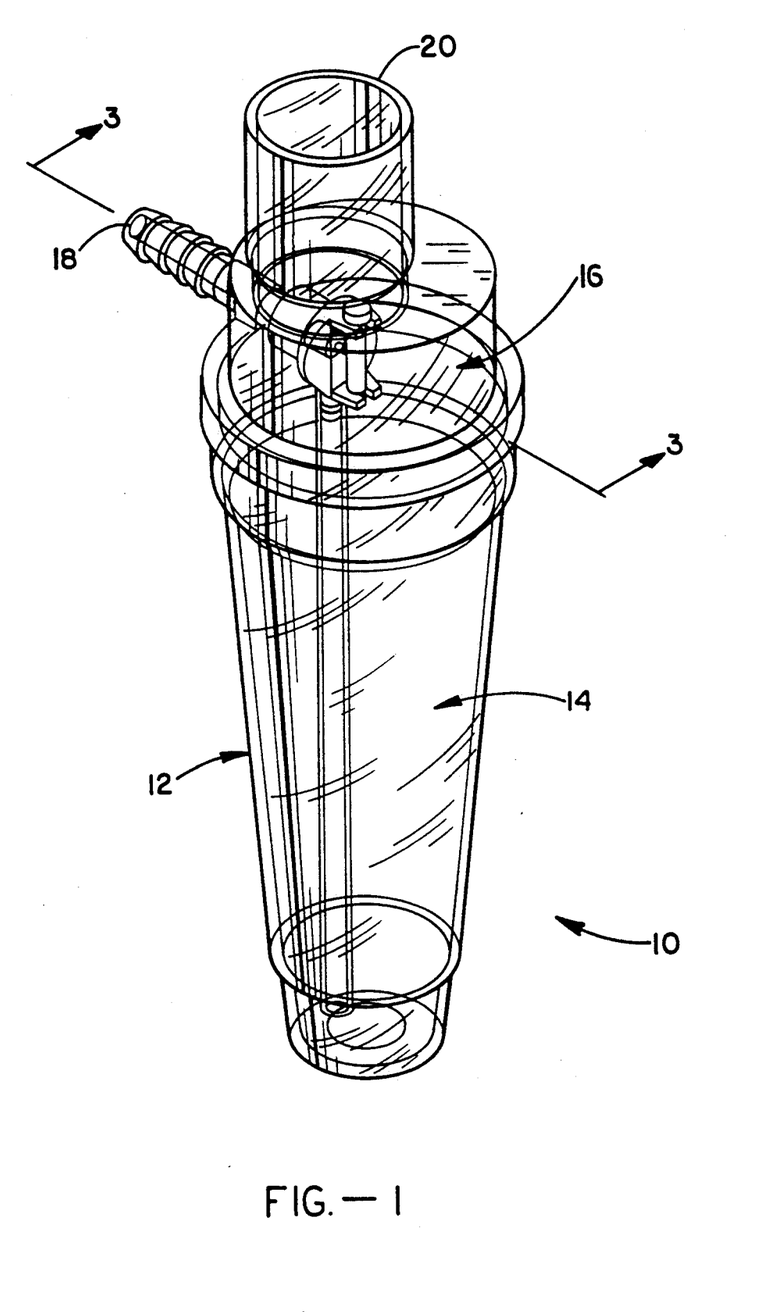
FIG. 1 is a perspective view of the nebulizer of the present invention.
Figure 2:
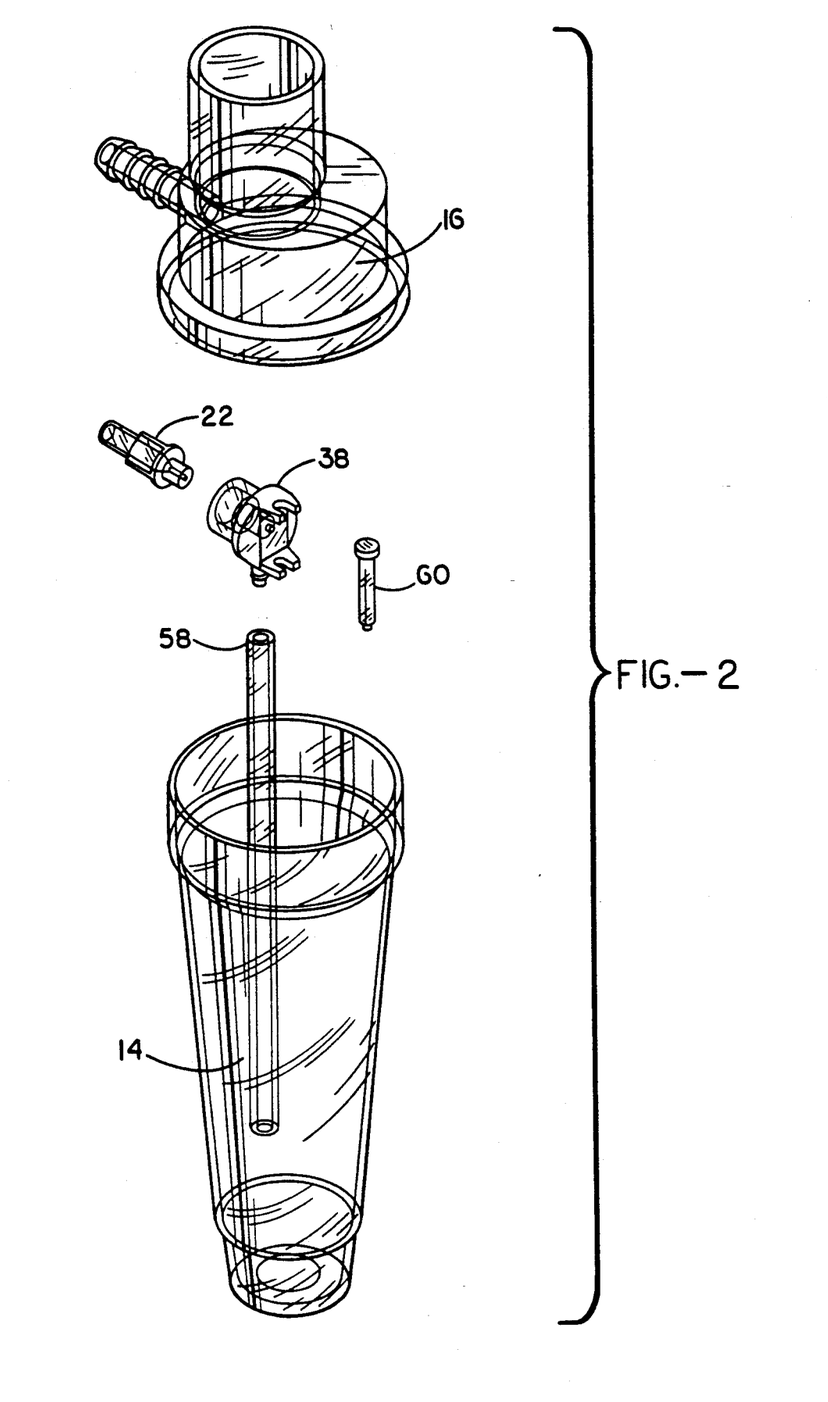
FIG. 2 is an exploded view of the nebulizer of the present invention.
Figure 3:
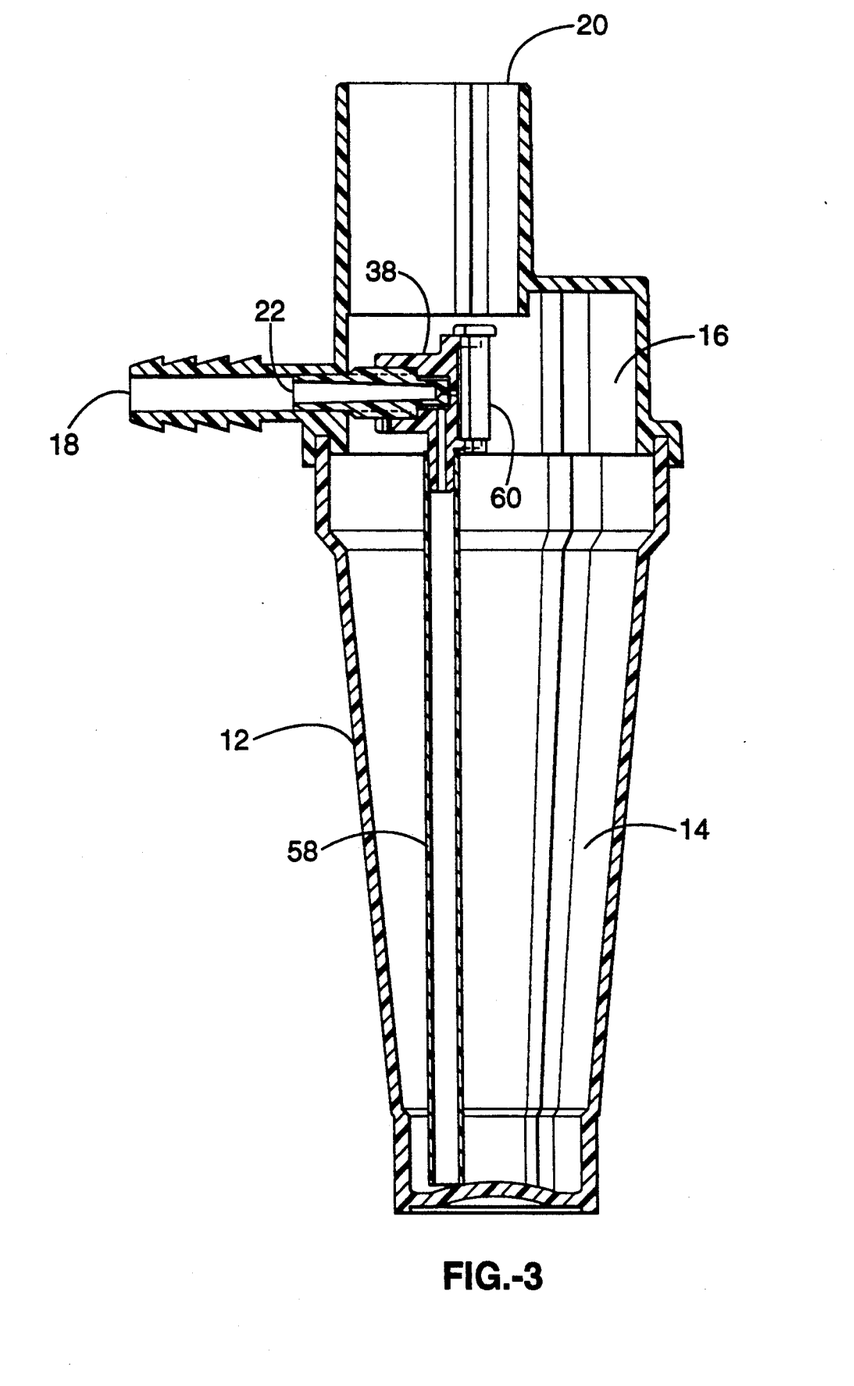
FIG. 3 is a cross-section view of the nebulizer shown in FIG. 1 taken through line 3—3.

Referring more specifically to the drawings, for illustrative purposes the present invention is embodied in the apparatus generally shown in FIG. 1 and shown in detail in FIG. 2 through FIG. 5. It will be appreciated that the apparatus may vary as to configuration and as to details of the parts without departing from the basic concepts as disclosed herein.

Referring to FIG. 1, the nebulizer 10 the present invention generally includes a housing 12 which serves as a reservoir with a lower fluid region 14 for containing fluid and an upper aerosol region 16 for containing nebulized fluid or aerosol generated by the device. The device accepts gas injected into gas inlet port 18, nebulizes fluid contained in lower fluid region 14 and exhausts the resultant aerosol through aerosol outlet port 20 which communicates with upper aerosol region 16.

Referring now to FIG. 2 through FIG. 5, coupled to housing 10 is a primary injector 22 which serves as a flow generating means. Primary injector 22, which serves as a gas injector, generally comprises a cylindrical body in which a primary orifice chamber 24 is interiorly disposed. One end of primary orifice chamber 24 opens toward gas inlet port 18, while the other end tapers to form a primary orifice 26 which extends from primary orifice chamber 24 to a gas outlet port 28 at the end of primary injector 22. The exterior diameter of primary injector 22 is reduced in the area of primary orifice 26 to form a nozzle 30. Radially disposed about gas outlet port 28 is a nozzle face 32 which is preferably a substantially planar circularly disposed surface. Compressed gas entering gas inlet port 18 is conducted through primary orifice chamber 24 and primary orifice 26 where it exits at gas outlet port 28 as a jet stream at the speed of sound and at a volumetric rate primarily controlled by the gas pressure and the diameter of primary orifice 26. The central portion of primary injector 22 includes a plurality of splines 34 radially projecting from its outer surface. An annular flange 36 projects outward from primary injector 22, and is disposed between splines 34 and nozzle 30.

A secondary injector 38 serves as a means to draw fluid from lower fluid region 14 and mix it with gas from primary injector 22. Secondary injector 38, which serves as a fluid injector, includes a central bore 40 which forms a secondary chamber 42 into which nozzle 30 extends. Flange 36 is so constructed as to mate firmly with a surface of secondary injector 38 surrounding bore 40 thereby sealing secondary chamber 42 against the escape of gas or fluid.

Secondary injector 38 includes a secondary orifice 44 which extends from a secondary orifice inlet port 46 in secondary chamber 42 to a secondary orifice outlet port 48 which opens into upper aerosol region 16. Radially disposed about secondary orifice inlet port 46 is a secondary orifice inlet face 50 which is preferably a generally planar circularly disposed surface. Radially disposed about secondary orifice outlet port is a secondary orifice outlet face 52 which is preferably a generally planar circularly disposed surface having a diameter of at least 7.6 millimeters. Preferably, nozzle face 32 and secondary orifice inlet face 50 are coplanar as shown. In addition, primary orifice 26 and secondary orifice 44 are aligned along a common central axis.

Figure 4:
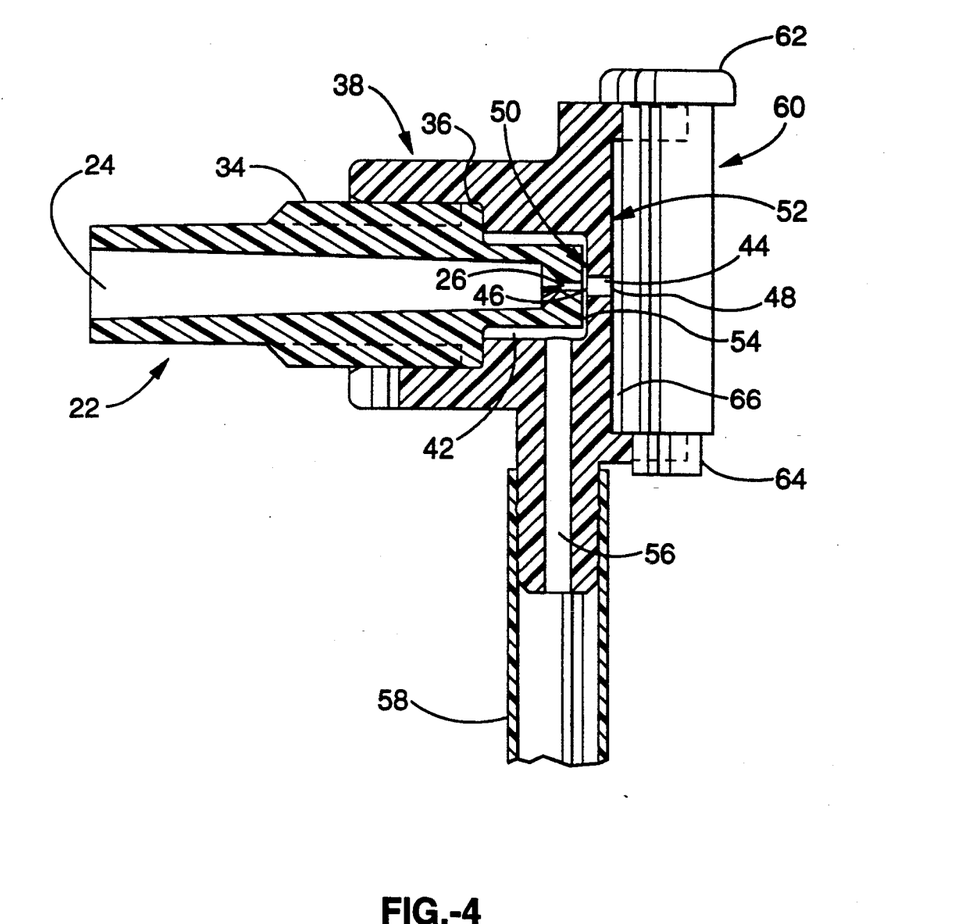
FIG. 4 is a detailed view of the nozzle portion of the nebulizer shown in the cross-section of FIG. 3.
Figure 5:
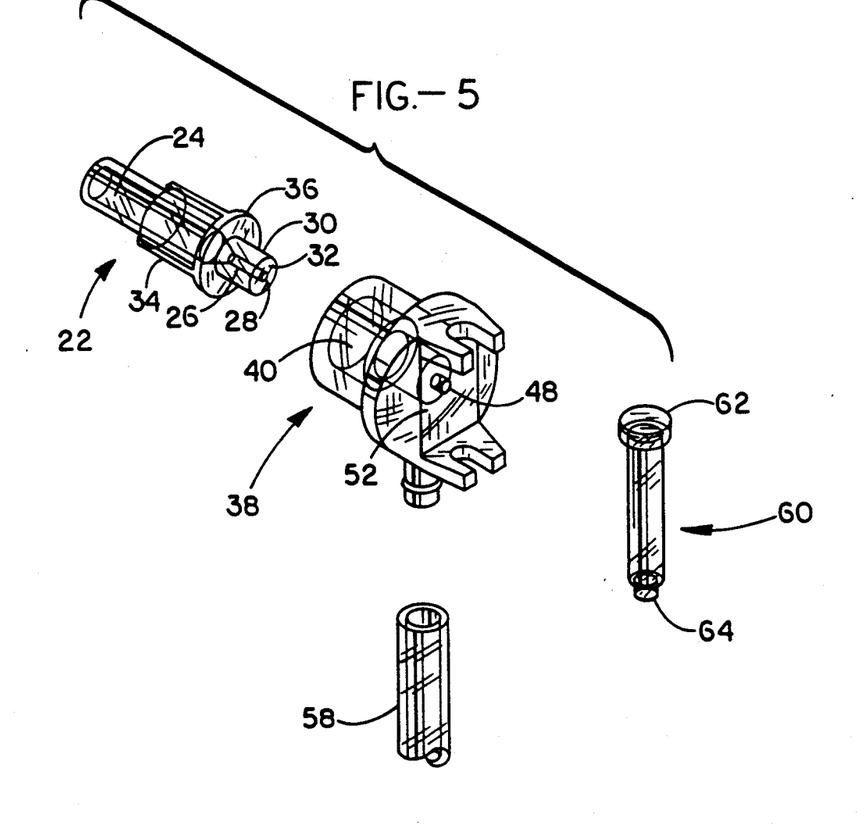
FIG. 5 is a front elevation view of the nebulizer shown in FIG. 1.

As can be seen in FIG. 4, when primary injector 22 is inserted into secondary injector bore 40, nozzle 30 extends into secondary chamber 42 and is spaced relation thereto thereby forming an inter-orifice gap 54 between nozzle face 32 and secondary orifice inlet face 50. In this manner, inter-orifice gap 54 separates primary orifice 26 from secondary orifice 44 and creates an area for fluid transfer to occur. Therefore, secondary chamber 42 generally comprises the area between nozzle face 32 and secondary orifice inlet face 50, as well as the area between the circumferential outer surface of nozzle 30 and the circumferential inner surface of bore 40 since the outer diameter of nozzle 30 is less than the inner diameter of bore 40. Secondary injector 38 also includes a fluid inlet port 56 which communicates with secondary chamber 42. A tube 58 coupled to fluid inlet port 56 and extending into lower fluid region 14 serves as a fluid conduit.

A non-spherical stagnation baffle 60 is positioned in upper aerosol region 16 and coupled to secondary injector 38 in proximity to secondary orifice outlet port 48. Preferably, stagnation baffle 60 is a cylindrical-shaped rod which is aligned with secondary orifice outlet port such that its longitudinal axis is perpendicular to the longitudinal axis of secondary orifice 44. A cap 62 and taper 64 at the upper and lower ends of stagnation baffle 60, respectively, assist in proper alignment. The distance between the surface of stagnation baffle 60 and secondary orifice outlet face 52 establishes a spray gap 66 which separates secondary orifice outlet port 48 from stagnation baffle 60.

When gas is injected into gas inlet port 18 at pressures ranging from 103 to 343 kilopascals (15 to 50 pounds per square inch gauge pressure) exits primary orifice 26, it creates a gas jet stream flowing at the speed of sound (sonic flow) which passes through the inter-orifice gap 54 and rapidly expands into the larger diameter secondary orifice 44. It should be noted that, while sonic flow is preferred, the apparatus can also operate at lower pressures which do not result in sonic flow of the gas jet stream. The expanding jet of gas entering the secondary orifice 44 creates a negative pressure in secondary chamber 42 which, being less than atmospheric pressure, creates a vacuum causing fluid to be drawn into secondary chamber. The stream of fluid is sheared in the inter-orifice gap in the area immediately surrounding secondary orifice inlet port 46 and broken into droplets of typically less than 100 micrometers in diameter which become entrained in the gas stream and mixed with the gas flowing through the secondary orifice 44.

The atomized fluid droplets then flow through secondary orifice 44 and spray gap 66, eventually striking stagnation baffle 60 where the larger droplets are further fragmented. Fluid droplets generally smaller than 4 micrometers in diameter are swept in the gas stream which exits spray gap 66 and forms the inhalable aerosol. The larger droplets accumulate on stagnation baffle 60 and fall back into lower fluid region 14 under the urge of gravity.

In order to assure the correct operation of the nebulizer and achieve the benefit of scalability to produce a dense cloud of uniformly small droplets at any specified flow rate or output volume, several specifications are required. First, the diameter of stagnation baffle 60 must fall between approximately 1.52 millimeters and approximately 4.83 millimeters. Second, the inter-orifice gap 54 must fall between approximately 0.10 millimeters and approximately 0.41 millimeters. Third, the secondary orifice 44 must have a length to diameter ratio between approximately 0.3 and approximately 1.7.

Fourth, the ratio of the diameter of secondary orifice 44 to primary orifice 26 must be between approximately 1.75 and approximately 3.25. Lastly, the spray gap 66 must be between approximately 0.23 millimeters and approximately 0.46 millimeters. By maintaining spray gap 66 within this range, capillarity (capillary action) will aid in the removal of droplets which accumulate on stagnation baffle 60. As a result of capillarity, the droplets will move toward the end of spray gap 66 where the fork- or rabbit ear-shaped standoffs (FIGS. 1, 2 and 5) used to couple stagnation baffle 60 to secondary injector 38, and eventually fall back into lower fluid region 14 under the urge of gravity. By adjusting any of the foregoing parameters its boundaries, the present invention is fully scalable to produce a selected flow rate or output volume for the aerosol generated.

A general optimization of the foregoing parameters can be achieved for operation at an input gas pressure of approximately 137.5 to 344 kilopascals (20 to 50 pounds per square inch gauge pressure), an output flow rate ranging from less than 1 liter per minute to approximately 2.25 liters per minute, and an output density ranging from approximately 35 to 55 microliters of aerosol per liter of gas. That optimization results where inter-orifice gap 54 is approximately 0.2 millimeters, spray gap 66 is approximately 0.33 millimeters, the diameter of stagnation baffle 60 is approximately 3.18 millimeters, the length to diameter ration of secondary orifice 44 is approximately 1.38 and the ratio of the diameter of secondary orifice 44 to primary orifice 26 is approximately 2.36.

Preferably the present invention is fabricated from a lightweight material such as plastic. Housing 12 is preferably transparent so that the amount of fluid in lower fluid region 14 can be readily observed. It should also be noted that housing 12 can be fitted with a port for injection of auxiliary medicines, and such a port could be coupled to an intravenous drip line or the like.

It can be seen, therefore, that the present invention provides a nebulizer which can produce the lower flow rates required for inhalation therapy of infants and children, and can be directly scaled to provide any flow rate or output volume within any given pressure range. Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A device for generating medicinal aerosols, comprising:
   (a) flow generating means for generating a jet of gas, said flow generating means including a primary orifice;
   (b) fluid reservoir means for holding fluid to be nebulized;
   (c) a fluid injector, said fluid injector coupled to said fluid reservoir means, said fluid injector coupled to said flow generating means, said fluid injector including a secondary orifice having an inlet and an outlet, said inlet of said secondary orifice spaced apart from and aligned with said primary orifice; and
   (d) stagnation baffle means for aerosolizing fluid droplets entrained in said gas upon striking said stagnation baffle means, said stagnation baffle means spaced proximally apart from said outlet of said secondary orifice by a gap ranging from approximately 0.23 millimeters to approximately 0.46 millimeters, said stagnation baffle means having a longitudinal axis aligned in a substantially perpendicular orientation in relation to a longitudinal axis extending through said secondary orifice.

2. An apparatus as recited in claim 1, wherein said spacing between said primary orifice and said secondary orifice is between approximately 0.10 millimeters and approximately 0.41 millimeters.

3. An apparatus as recited in claim 2, wherein a diameter of said secondary orifice is between approximately 1.75 and approximately 3.25 times larger than a diameter of said primary orifice.

4. An apparatus as recited in claim 3, wherein said secondary orifice has a length to diameter ratio between approximately 0.3 and approximately 1.7.

5. An apparatus as recited in claim 4, wherein said stagnation baffle means has a diameter between approximately 1.52 millimeters and approximately 4.83 millimeters.

6. A nebulizer, comprising:
(a) gas injector means for generating a jet of gas at a sonic flow rate, said gas injector means including a primary orifice having a gas outlet at one end;
(b) fluid reservoir means for holding fluid to be nebulized;
(c) a fluid injector, said fluid injector coupled to said fluid reservoir means, said fluid injector coupled to said gas injector means, said fluid injector including a secondary orifice having an inlet and outlet, said inlet of said secondary orifice spaced apart from and aligned with said gas outlet; and
(d) a generally cylindrical-shaped stagnation baffle means for aerosolizing fluid droplets entrained in said gas upon striking said stagnation baffle means, said stagnation baffle means spaced proximally apart from said outlet of said secondary orifice by a gap ranging from approximately 0.23 millimeters to approximately 0.46 millimeters, said stagnation baffle means having a longitudinal axis aligned in a substantially perpendicular orientation in relation to a longitudinal axis extending through said secondary orifice.

7. An apparatus as recited in claim 6, wherein said gas injector includes a substantially planar nozzle face radially disposed about said gas outlet.

8. An apparatus as recited in claim 7, wherein said fluid injector includes a substantially planar inlet face radially disposed about said inlet of said secondary orifice, said inlet face opposing said nozzle face.

9. An apparatus as recited in claim 8, wherein said fluid injector includes a substantially planar outlet face radially disposed about said outlet of said secondary orifice, said outlet face opposing said stagnation baffle means.

10. An apparatus as recited in claim 6, wherein said stagnation baffle has a diameter between approximately 1.52 millimeters and approximately 4.83 millimeters, said spacing between said primary orifice and said secondary orifice is between approximately 0.10 millimeters and approximately 0.41 millimeters, said secondary orifice has a length to diameter ratio between approximately 0.3 and approximately 1.7, and said secondary orifice has a diameter between approximately 1.75 and approximately 3.25 times larger than a diameter of said primary orifice.

11. An apparatus for generating an aerosol of fluid droplets dispersed in a gaseous flow, comprising:
(a) a housing, said housing including a lower fluid containment means for containing a fluid to be nebulized, an upper aerosol containment means for containing nebulized fluid, and an aerosol outlet port communicating with said upper aerosol containment means;
(b) a primary injector coupled to said housing, said primary injector including a gas inlet port and a primary orifice;
(c) a secondary injector coupled to said primary injector, said secondary injector including a fluid inlet port, a secondary orifice, and a secondary chamber, said secondary orifice extending between said secondary chamber and said upper reservoir region, said primary injector disposed within said secondary chamber to form a gap between said primary orifice and said secondary orifice, said primary orifice axially aligned with said secondary orifice;
(d) a non-spherical stagnation baffle means, coupled to said secondary injector, for aerosolizing fluid droplets entrained in said gas upon striking said stagnation baffle means, said stagnation baffle means having a surface positioned in proximity to said secondary orifice by a gap ranging from approximately 0.23 millimeters to approximately 0.46 millimeters, said stagnation baffle means having a longitudinal axis aligned in a substantially perpendicular orientation in relation to a longitudinal axis extending through said secondary orifice;
(e) a conduit, said conduit extending from said fluid inlet port into said lower fluid containment means.

12. An apparatus as recited in claim 11, further comprising a generally planar outlet surface, said outlet surface positioned in said upper aerosol containment means, said outlet surface radially disposed about said secondary orifice, said outlet surface opposing said stagnation baffle means surface.

13. An apparatus as recited in claim 12, wherein said primary injector includes a generally planar nozzle surface radially disposed about said primary orifice.

14. An apparatus as recited in claim 13, wherein said secondary chamber includes a generally planar inlet surface radially disposed about said secondary orifice.

15. An apparatus as recited in claim 14, wherein said nozzle surface and said inlet surface are substantially coplanar.

16. An apparatus as recited in claim 15, wherein said stagnation baffle means is generally cylindrical-shaped.

17. An apparatus as recited in claim 11, wherein said gap between said primary orifice and said secondary orifice is between approximately 0.10 millimeters and approximately 0.41 millimeters.

18. An apparatus as recited in claim 17, wherein a diameter of said secondary orifice is between approximately 1.75 and approximately 3.25 times larger than a diameter of said primary orifice.

19. An apparatus as recited in claim 18, wherein said secondary orifice has a length to diameter ratio between approximately 0.3 and approximately 1.7.

20. An apparatus as recited in claim 19, wherein said stagnation baffle means has a diameter between approximately 1.52 millimeters and approximately 4.83 millimeters.

21. A scalable nebulizing device for generating medicinal aerosols for delivery to a patient, comprising:

(a) a primary injector, said primary injector including a gas inlet port and a gas outlet port, said primary injector including a gas outlet face circularly disposed about said gas outlet port;

(b) a secondary injector, said secondary injector including a fluid inlet port, said secondary injector including an orifice having an inlet port and an outlet port, said orifice including an orifice inlet face circularly disposed about said orifice inlet port, said orifice including an orifice outlet face circularly disposed about said orifice outlet port, said secondary injector including a chamber, said primary injector extending into said chamber to form a gap between said gas outlet face and said orifice inlet face, said gas outlet port axially aligned with said orifice inlet port;

(c) a generally rod-shaped stagnation baffle means for aerosolizing fluid droplets entrained in said gas upon striking said stagnation baffle means, said stagnation baffle means having a surface positioned in proximity to said orifice outlet port to form a spray gap between said orifice outlet face and said surface of said stagnation baffle means ranging from approximately 0.23 millimeters to approximately 0.46 millimeters, said stagnation baffle means having a longitudinal axis aligned in a substantially perpendicular orientation in relation to a longitudinal axis extending through said secondary orifice;

(d) a housing, said housing coupled to said primary injector, said housing including a reservoir, said reservoir including a lower fluid region and an upper aerosol region; and (e) a tube, said tube coupled to said fluid inlet port, said tube extending into said lower fluid region of said reservoir.

22. An apparatus as recited in claim 21, wherein said gap between said gas outlet face and said orifice inlet face is between 0.10 millimeters and 0.41 millimeters.

23. An apparatus as recited in claim 22, wherein a diameter of said orifice inlet port is between approximately 1.75 and approximately 3.25 times larger than a diameter of said gas outlet port.

24. An apparatus as recited in claim 23, wherein said orifice has a length to diameter ratio between 0.3 and 1.7.

25. An apparatus as recited in claim 24, wherein said stagnation baffle means has a diameter between approximately 1.52 millimeters and approximately 4.83 millimeters.

* * * * *